(12) United States Patent
Steffen et al.

(10) Patent No.: US 8,306,600 B2
(45) Date of Patent: Nov. 6, 2012

(54) FILTER SET FOR OBSERVING FLUORESCENCE RADIATION IN BIOLOGICAL TISSUE

(75) Inventors: Joachim Steffen, Westhausen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 421 days.

(21) Appl. No.: 12/506,016

(22) Filed: Jul. 20, 2009

(65) Prior Publication Data

US 2010/0044583 A1 Feb. 25, 2010

(30) Foreign Application Priority Data

Jul. 21, 2008 (DE) .......................... 10 2008 034 008

(51) Int. Cl.
*A61B 5/00* (2006.01)

(52) U.S. Cl. ........ 600/407; 600/476; 356/416; 356/419; 359/885

(58) Field of Classification Search .................. 600/407, 600/473, 475–478; 356/416, 419, 432; 359/885, 359/889
See application file for complete search history.

(56) References Cited

U.S. PATENT DOCUMENTS

| | | | |
|---|---|---|---|
| 5,127,730 A | 7/1992 | Brelje et al. | |
| 5,306,144 A | 4/1994 | Hibst et al. | |
| 5,507,287 A | 4/1996 | Palcic et al. | |
| 6,212,425 B1 | 4/2001 | Irion et al. | |
| 6,583,873 B1 | 6/2003 | Goncharov et al. | |
| 6,667,830 B1 | 12/2003 | Iketaki et al. | |
| 6,899,675 B2 | 5/2005 | Cline et al. | |
| 2004/0109231 A1 | 6/2004 | Haisch et al. | |
| 2004/0234417 A1 | 11/2004 | Schienle et al. | |
| 2006/0291772 A1 | 12/2006 | Haiml et al. | |
| 2007/0160500 A1 | 7/2007 | Baumfalk et al. | |

FOREIGN PATENT DOCUMENTS

| | | |
|---|---|---|
| DE | 33 00 517 A1 | 7/1984 |
| DE | 199 48 391 A1 | 4/2001 |
| DE | 103 39 784 A1 | 3/2004 |
| DE | 102 01 005 B4 | 3/2007 |
| DE | 10 2005 048 187 A1 | 4/2007 |
| DE | 10 2005 048 188 A1 | 4/2007 |
| DE | 10 2006 015 272 A1 | 10/2007 |
| DE | 698 37 839 T2 | 12/2007 |
| DE | 10 2006 047 911 A1 | 4/2008 |
| EP | 0 195 375 A2 | 9/1986 |
| EP | 0 517 516 A1 | 12/1992 |
| EP | 0 803 724 A2 | 10/1997 |
| EP | 0 816 829 A2 | 1/1998 |
| EP | 0 861 044 B1 | 2/1998 |
| EP | 0 899 558 A2 | 3/1999 |
| EP | 1 177 761 A2 | 2/2002 |
| EP | 1 306 663 A2 | 5/2003 |
| EP | 1 731 087 A2 | 12/2006 |
| GB | 2 254 417 A | 10/1992 |
| WO | WO 92/02839 A1 | 2/1990 |
| WO | WO 92/15008 A1 | 9/1992 |
| WO | WO 97/23648 A1 | 7/1997 |
| WO | WO 98/39636 A1 | 9/1998 |

*Primary Examiner* — Ruth S Smith
(74) *Attorney, Agent, or Firm* — Potomac Patent Group PLLC

(57) ABSTRACT

A filter set for observing fluorescent radiation in biological tissue includes at least one illumination filter and at least one observation filter. The at least one illumination filter is arrangeable in an illumination system of an optical system. The at least one least one observation filter is arrangeable in an imaging system of the optical system.

48 Claims, 6 Drawing Sheets

FILTER SET FOR OBSERVING FLUORESCENCE RADIATION IN BIOLOGICAL TISSUE

CROSS-REFERENCES TO RELATED APPLICATIONS

This application claims priority to German Patent Application DE 10 2008 034 008.1, filed Jul. 21, 2008. The disclosure of DE 10 2008 034 008.1 is hereby incorporated by reference in its entirety for all purposes.

BACKGROUND OF THE INVENTION

1. Field of the Invention

The invention relates to a filter set for observing fluorescent radiation (also called fluorescence radiation; radiation caused by fluorescence) in biological tissue and thus relates to observing emission of light of an endogenous (produced naturally in the body) or exogenous fluorophore due to an excitation using radiation. Herein, fluorophore in general refers to a substance for which fluorescence (emission of fluorescent radiation) arises due to an excitation. The observation may optionally be performed in a living organism and thus in vivo or in an artificial environment (outside of living organisms, for example in vitro). Further, the invention relates to a medical optical system comprising this filter set and a method of selecting filters of a filter set.

2. Brief Description of the Related Art

Such filter sets in particular are employed in optical systems of medical technology, such as for example microscopes or endoscopes that are adapted for observing fluorescent radiation (e.g. fluorescence microscopes).

To release fluorescence in biological tissue a fluorescent dye is applied to a patient, for example. This fluorescent dye may be chosen such that it is enriched in tumour tissue in an enhanced concentration. For diagnosis, the tissue to be examined is illuminated with excitation radiation after application of the fluorescent dye. This excitation radiation has to be chosen in dependence of an excitation band (a spectral band of the excitation radiation) of the used fluorescent dye in an appropriate way. Due to the excitation radiation, spontaneous emission of fluorescent radiation arises in the fluorescent dye. The intensity of the fluorescent radiation depends on the used fluorescent dye, the excitation band, the intensity of the excitation radiation and the enrichment of the fluorescent dye within the tissue. The fluorescent band (spectral band of the fluorescent radiation, also called fluorescence band) of the fluorescent radiation also depends on the used fluorescent dye. The excitation bands of a fluorescent dye always lie at smaller wavelengths than the associated fluorescent bands.

In this way a tumour, for example, may be marked and localized using the fluorescent radiation.

Since the intensity of the fluorescent radiation is usually more than one order of magnitude smaller than the intensity of the excitation radiation, there is the risk that the fluorescent radiation is outshone by the excitation radiation. Consequently, excitation radiation is usually used comprising a wavelength range which does not overlap with the wavelength range of the fluorescent radiation. By filtering the excitation radiation from an observation beam path the fluorescent radiation may be separated from the excitation radiation and may be observed.

Thus, a compromise between an optimal excitation of the fluorescence (by excitation of the fluorescent dye/fluorophore) by exploiting the excitation band to a wide extent and a prevention of outshining the fluorescent radiation caused by the fluorescence (and thus of a good optical opportunity to distinguish excitation band and fluorescent band) is aimed for.

Known fluorescent dyes employable in medical technology are for example Indocyanine green, Protoporphyrin IX and Hypericin. The excitation band of Indocyanine green lies at 400 nm to 780 nm and the fluorescent band lies at about 830 nm. The excitation band of Protoporphyrin IX lies at about 400 nm and the fluorescent band lies between about 630 nm and 730 nm. Hypericin has three excitation bands at 467 nm, 550 nm, and 594 nm as well as two fluorescent bands at 600 nm and 650 nm. The preceding fluorescent dyes further exhibit, beside a high intensity of the fluorescent radiation and a sufficient distance between the respective excitation band and the fluorescent band, a good compatibility and degradability of the fluorescent dye in the human organism.

The excitation bands and the fluorescent bands of Hypericin are exemplarily shown in FIG. 1. In FIG. 1 the solid line denotes the excitation spectrum and the broken line denotes the fluorescence spectrum (also called fluorescent spectrum) of Hypericin. FIG. 1 was obtained in a cell culture medium at a concentration of 1 µM.

As an alternative to applying a fluorescent dye, a so called auto-fluorescence of the tissue may be exited caused by organism endogenous (organic endogenous) fluorescent material.

During observing fluorescent radiation in biological tissue it is desirable that, in addition to observing the fluorescent radiation, it is also possible to observe tissue which is adjacent to tissue emitting the fluorescent radiation. This facilitates, on one hand, the differentiation of diseased and healthy tissue and, on the other hand, the localisation of the diseased tissue in the surrounding healthy tissue. Otherwise there is for example the risk that, although tumour tissue may be observed using the fluorescent radiation, it may not be sufficiently localized in the surrounding tissue and that it may not be sufficiently differentiated from healthy tissue. The observation of the adjacent tissue may be performed in a colour (and thus in a spectral band), which differs from the colour of the fluorescence (the observed fluorescent band).

For observing fluorescent radiation in biological tissue a microscopy system having an illumination system and an observation system adapted to the fluorescence of Indocyanine green is known from German published application DE 103 39 784 A1, the content of which is herewith incorporated by reference.

From European Patent EP 0 861 044 B1 an apparatus for diagnosis using a reaction in biological tissue caused by a light induced photosensibilisator (photosensitizer) or by endogenous fluorescence is known. The preceding apparatus is in particular suitable for the use of Delta-Aminolevulinic-Acid (ALA) as fluorescent dye.

For the known solutions, deficiencies may occur depending on the fluorescent dye used when observing at the same time the fluorescent radiation and tissue which is adjacent to the tissue emitting the fluorescent radiation. In particular, the known solutions are suitable to only a limited extent for fluorescent dyes for which the excitation band and the fluorescent band lie very close to each other or partially overlap (as is for example the case for Hypericin).

BRIEF SUMMARY OF THE INVENTION

The present invention has been accomplished taking the above problems into consideration.

Embodiments are directed, to provide a filter set for observing fluorescence in biological tissue which filter set is universally usable and which allows, additionally to observing the fluorescent radiation itself, observing tissue which is adjacent to tissue emitting the fluorescent radiation.

Further, embodiments are directed to a filter set which is in particular suitable for fluorescent dyes for which the excitation band and the fluorescent band lie very close to each other or partially overlap.

According to a first embodiment a filter set for observing fluorescent radiation in biological tissue comprises at least one illumination filter and at least one observation filter. Herein, the at least one illumination filter is arrangeable in an illumination system of an optical system and has a first wavelength transmission range and has a first wavelength blocking range comprising wavelengths longer than those comprised in the first wavelength transmission range. The at least one observation filter however is arrangeable in an imaging system of an optical system and has a second wavelength transmission range comprising wavelengths longer than those comprised in the first wavelength transmission range of the at least one illumination filter and has a second wavelength blocking range comprising wavelengths shorter than those comprised in the second wavelength transmission range. A transmittance for wavelengths both in the first and the second wavelength transmission ranges is greater than 0.5 and in particular greater than 0.8, and is smaller than 0.5 and in particular smaller than 0.2 both in the first and the second wavelength blocking ranges.

Herein, the transmittance for wavelengths (which is also denoted as "spectral transmittance") is defined as a ratio of radiation power at a particular wavelength behind an obstacle (such as for example a filter) and a radiation power of the same wavelength in front of the obstacle. The radiant power Φ (also denoted as "radiant flux") is defined as the radiation energy dQ which is transported by electromagnetic waves per time interval dt:

$$\Phi = \frac{dQ}{dt}$$

A product of the transmittance for wavelengths of the at least one illumination filter and the transmittance for wavelengths of the at least one observation filter both in the second wavelength transmission range and in the second wavelength blocking range is smaller than 0.05. The illumination filter and the observation filter thus exclude each other in these ranges to a large extent, wherein however a certain overlap of the first wavelength transmission range of the illumination filter with the second wavelength transmission range of the observation filter is not completely excluded.

Further, the at least one observation filter has a third wavelength transmission range comprising wavelengths shorter than those comprised in the second wavelength blocking range. The first, the second, and the third wavelength transmission ranges as well as the first and the second wavelength blocking ranges comprise the spectral range from 350 nm to 780 nm and thus each comprise at least partially the spectral range of visible light. In other words, none of the aforementioned wavelength transmission ranges and wavelength blocking ranges lies entirely outside of the spectral range of visible light.

Further, the at least one illumination filter and the at least one observation filter are adapted such that they commonly satisfy the dimensioning rule $$X < \int_{350}^{Z} T_L(\lambda) \cdot T_O(\lambda) d\lambda < Y.$$

Thereby, $T_L(\lambda)$ is the transmittance for wavelengths λ of the at least one illumination filter (wavelengths dependent transmittance), $T_O(\lambda)$ is the transmittance for wavelengths λ of the at least one observation filter (wavelengths dependent transmittance), $X \geqq 0.02$ nm, $Y \leqq 5$ nm, and Z is a predetermined wavelength between 480 nm and 595 nm (480 nm$\leqq Z \leqq$595 nm). In other words the at least one illumination filter and the at least one observation filter are adapted such that the integral over the product of the transmittance for wavelengths of the at least one illumination filter and the transmittance for wavelengths of the at least one observation filter taken over wavelengths from 350 nm up to a value Z of minimally 480 nm and maximally 595 nm lies in a range from X being at least 0.02 nm to Y being at most 5 nm. Thus, the area below the curve of the product of the transmittances for wavelengths of the at least one illumination filter and the observation filter in the range from 350 nm up to at most Z=595 nm amounts to between a predetermined minimum value X and a maximum value Y. Thereby, the minimum value X ensures that for observing non-fluorescent tissue over all wavelengths in the range enough light is provided, whereas the maximum value Y ensures that the fluorescent radiation is not outshone. In this way it is ensured that concurrent observing the fluorescence as well as also observing surrounding tissue is possible.

According to an embodiment $X \geqq 0.04$ nm and in particular $X \geqq 0.05$ nm holds. According to a further embodiment $Y \leqq 3$ nm and in particular $Y \leqq 1.5$ nm holds. Further, according to an embodiment $Z \geqq 500$ nm and in particular $570 \leqq Z \leqq 585$ nm holds.

According to a second alternative embodiment a filter set for observing fluorescent radiation in biological tissue comprises at least one illumination filter and at least one observation filter. The at least one illumination filter is arrangeable in an illumination system of an optical system and has a first wavelength transmission range and a first wavelength blocking range comprising wavelengths longer than those comprised in the first wavelength transmission range. The at least one observation filter is arrangeable in an imaging system of an optical system. The at least one observation filter has a second wavelength transmission range comprising wavelengths longer than those comprised in the first wavelength transmission range of the at least one illumination filter and has a second wavelength blocking range comprising wavelengths shorter than those comprised in the second wavelength transmission range. A transmittance for wavelengths both in the first and the second wavelength transmission ranges is greater than 0.5 and in particular greater than 0.8, and a transmittance for wavelengths both in the first and the second wavelength blocking ranges is smaller than 0.5 and in particular smaller than 0.2. A product of the transmittance of wavelengths of the at least one illumination filter and the transmittance for wavelengths of the at least one observation filter both in the second wavelength transmission range and the second wavelength blocking range is smaller than 0.05. Also in this embodiment the at least one observation filter has a third wavelength transmission range comprising wavelengths shorter than those comprised in the second wavelength blocking range.

The transmittance for wavelengths of the at least one observation filter is, according to the second embodiment, in the third wavelength transmission range greater than 0.01 and in the second wavelength blocking range is smaller than 0.01. The second wavelength blocking range has a spectral width of at least 100 nm. In other words the third wavelength transmission range is spaced apart compared to the second wavelength transmission range towards smaller wavelengths by an amount of the second wavelength blocking range with a spectral width of at least 100 nm. Consequently, radiation transmitted by the third wavelength transmission range has a significantly different colour compared to radiation transmitted by the second wavelength transmission range. The first, the second, and the third wavelength transmission ranges as well as and the first and the second wavelength blocking ranges at least partially each comprise the spectral range from 350 nm to 780 nm.

According to an embodiment a product of the transmittance for wavelengths of the at least one illumination filter and the transmittance for wavelengths of the at least one observation filter in the third wavelength transmission range within a predetermined spectral band of less than 60 nm and in particular less than 40 nm and further in particular of not more than 20 nm is greater than 0.004 and is smaller than 0.004 outside of this spectral band. In other words the third wavelength transmission range and the first wavelength transmission range overlap for less than 60 nm and in particular less than 40 nm and in particular for not more than 20 nm.

Further, according to an embodiment, a product of the transmittance for wavelengths of the at least one illumination filter and the transmittance for wavelengths of the at least one observation filter within a predetermined spectral band from 400 nm to 460 nm and in particular from 410 nm to 450 nm and further in particular from 420 nm to 440 nm is greater than 0.004 and is smaller than 0.004 outside of this spectral band. In other words the first and the third wavelength transmission ranges overlap in the given range. The centre of the overlap may for example lie at 430 nm.

Further, the product of the transmittance for wavelengths of the at least one illumination filter and the transmittance for wavelengths of the at least one observation filter may have, according to an embodiment, within the aforementioned predetermined spectral band a maximum greater than 0.005 and in particular greater than 0.0075 and further in particular equal to 0.01.

The product of the transmittance for wavelengths of the at least one illumination filter and the transmittance for wavelengths of the at least one observation filter may have, according to an embodiment, within the aforementioned predetermined spectral band a maximum of smaller than 0.05 and in particular smaller than 0.025 and further in particular equal to 0.01.

According to an embodiment the transmittance for wavelengths of the at least one observation filter in the third wavelength transmission range for wavelengths smaller than 450 nm and in particular wavelengths smaller than 435 nm and further in particular wavelengths smaller than 420 nm and further in particular wavelengths smaller than 410 nm is greater than 0.01 and is smaller than 0.01 for longer wavelengths. Thereby, according to an embodiment, the transmittance for wavelengths in the third wavelength transmission range may be greater than 0.5 and in particular greater than 0.8. Thus, the at least one observation filter may, considered altogether, have a high transmittance for short and long wavelengths, and may have a low transmittance for medium wavelengths, and thus may be composed for example from two single filters. Further, the first wavelength transmission range of the illumination filter may largely be arranged in the medium wavelength range in which the at least one observation filter has a low transmittance for wavelengths.

According to a third alternative embodiment the filter set for observing fluorescent radiation in biological tissue comprises at least one illumination filter and at least one observation filter. The at least one illumination filter is, as in the other embodiments, arrangeable in an illumination system of an optical system and has a first wavelength transmission range and a first wavelength blocking range comprising wavelengths longer than those comprised in the first wavelength transmission range. The at least one observation filter is arrangeable in an imaging system of the optical system and has a second wavelength transmission range comprising wavelengths longer than those comprised in the first wavelength transmission range of the at least one illumination filter and has a second wavelength blocking range comprising wavelengths shorter than those comprised in the second wavelength transmission range. A transmittance for wavelengths both in the first and the second wavelength transmission ranges is greater than 0.5 and in particular greater than 0.8 and both in the first and the second wavelength blocking ranges is smaller than 0.5 and in particular smaller than 0.2. A product of the transmittance for wavelengths of the at least one illumination filter and the transmittance for wavelengths of the at least one observation filter both in the second wavelength transmission range and in the second wavelength blocking range is smaller than 0.05. The at least one observation filter has for wavelengths smaller than those comprised in the second wavelength blocking range further a third wavelength transmission range, wherein the transmittance for wavelengths of the at least one observation filter in the third wavelength transmission range across a spectral width of at least 20 nm is greater than 0.001 and is smaller than 0.001 in the second wavelength blocking range. Thus, the third wavelength transmission range has a relatively low transmittance. The second wavelength blocking range has a spectral width of at least 30 nm so that the second wavelength transmission range and the third wavelength transmission range are spectrally spaced apart at least 30 nm. The first, the second, and the third wavelength transmission ranges and the first and the second wavelength blocking ranges each at least partially comprise the spectral range from 350 nm to 780 nm.

According to an embodiment the third wavelength transmission range of the at least one observation filter may entirely lie within the first wavelength transmission range of the at least one illumination filter. Due to the relatively low transmittance for wavelengths in the third wavelength transmission range the risk of outshining a fluorescent radiation is low in spite of the spectral width of the third wavelength transmission range and in spite of the relatively high transmittance for wavelengths in the first wavelength transmission range.

A product of the transmittance for wavelengths of the at least one illumination filter and the transmittance for wavelengths of the at least one observation filter may, according to an embodiment, in the third wavelength transmission range within a predetermined spectral band of at least 20 nm and in particular at least 40 nm and further in particular at least 60 nm be greater than 0.001 and may be smaller than 0.001 outside of this spectral band. In other words the third wavelength transmission range and the first wavelength transmission range overlap for at least 20 nm and in particular at least 40 nm and further in particular for at least 60 nm.

According to an embodiment a product of the transmittance for wavelengths of the at least one illumination filter and the transmittance for wavelengths of the at least one observation filter may in the third wavelength transmission range within a predetermined spectral band of less than 100 nm and in particular less than 90 nm and further in particular less than 80 nm be greater than 0.001 and may be smaller than 0.001 outside of this spectral band. Consequently, the third wavelength transmission range and the first wavelength transmission range overlap for less than 100 nm and in particular less than 90 nm and further in particular less than 80 nm. According to an embodiment, the third wavelength transmission range is arranged completely or partially within the first wavelength transmission range.

A product of the transmittance for wavelengths of the at least one illumination filter and the transmittance for wavelengths of the at least one observation filter may, according to an embodiment, within a predetermined spectral band from 350 nm to 590 nm and in particular 400 nm to 510 nm and in particular 410 nm to 500 nm and further in particular 420 nm to 490 nm be greater than 0.001, and may be smaller than 0.001 outside of this spectral band. Thus, the first and the third wavelength transmission ranges overlap in this range.

Further, according to an embodiment, a product of the transmittance for wavelengths of the at least one illumination filter and the transmittance for wavelengths of the at least one observation filter may have a maximum of greater than 0.0015 and in particular greater than 0.002 and further in particular equal to 0.0025 within the third wavelength transmission range or the aforementioned predetermined spectral band.

Further, the transmittance for wavelengths of the at least one observation filter may, according to an embodiment, be greater than 0.001 in the third wavelength transmission range for ranges of wavelengths from 350 nm to 590 nm and in particular 400 nm to 510 nm and in particular from 410 nm to 500 nm and further in particular from 420 nm to 490 nm, and may be smaller than 0.001 outside of these ranges.

According to an embodiment the second wavelength blocking range has a spectral width of at least 45 nm and in particular of at least 65 nm and further in particular of at least 80 nm. Thus, fluorescent radiation transmitted by the second wavelength transmission range of the at least one observation filter and radiation transmitted by the third wavelength transmission range may lie in significantly different spectral ranges and may have different colors.

The transmittance for wavelengths of the at least one observation filter in the second wavelength blocking range is, according to an embodiment, smaller than 0.001 and in particular smaller than 0.0005 and further in particular smaller than 0.0001. Thus, radiation transmitted by the second wavelength blocking range of the at least one observation filter may for example have a significantly lower intensity than fluorescent radiation transmitted by the second wavelength transmission range.

According to an embodiment a product of the transmittance for wavelengths of the at least one illumination filter and the transmittance for wavelengths of the at least one observation filter in a spectral range, between the first wavelength transmission range and the second wavelength transmission range, of at least 3 nm and in particular of at least 5 nm and further in particular of at least 10 nm of spectral width is smaller than 0.05. Consequently, the first and the second wavelength transmission ranges are spaced apart accordingly.

A product of the transmittance for wavelengths of the at least one illumination filter and the transmittance for wavelengths of the at least one observation filter is, according to an embodiment, both in the second wavelength transmission range and the second wavelength blocking range, smaller than 0.01 and in particular smaller than 0.0075 and in particular smaller than 0.005 and further in particular smaller than 0.001. Thus, radiation transmitted by the at least one illumination filter in the first wavelength transmission range is almost entirely filtered out in the second wavelength blocking range by the at least one observation filter. Further, the at least one illumination filter transmits almost no radiation of the second wavelength transmission range of the at least one observation filter.

According to an embodiment the transmittance for wavelengths of the at least one illumination filter in the first transmission range for ranges of wavelength from 415 nm to 595 nm and in particular from 425 nm to 590 nm and further in particular from 435 nm to 585 nm is greater than 0.5 and in particular greater than 0.8, and is smaller than 0.5 outside of these ranges and thus outside of the first wavelength transmission range.

Further, the transmittance for wavelengths of the at least one observation filter in the second wavelength transmission range for wavelengths greater than 585 nm and in particular for wavelengths greater than 590 nm and further in particular for wavelengths greater than 595 nm is, according to an embodiment, greater than 0.5 and in particular greater than 0.8, and is smaller than 0.5 for smaller wavelengths and thus below the second wavelength transmission range.

The transmittance for wavelengths of the at least one illumination filter in the first wavelength transmission range is, according to an embodiment, greater than 0.9 and in particular greater than 0.95. Additionally or alternatively, according to this embodiment, the transmittance for wavelengths of the at least one observation filter in the second wavelength transmission range is greater than 0.9 and in particular greater than 0.95.

In all embodiments the filters may for example be formed as at least one of transmission filters and reflection filters.

According to an embodiment, an optical system of medical technology (medical system) is adapted for observing fluorescent radiation in biological tissue. The medical optical system may for example be a microscope, in particular a surgical microscope, or an endoscope. The system comprises an illumination system having a light source and illumination optics, to illuminate the tissue with illumination radiation. For example, the light source may be a xenon light source or a halogen light source emitting white light having a broad band spectrum. Further, the system comprises an imaging system having imaging optics, to guide radiation emanating from the tissue to an image plane. In this way the tissue may be imaged into the image plane. The system further comprises the previously described filter set. Thereby, the illumination system comprises at least one filter holder with the at least one illumination filter of the filter set, and the imaging system comprises at least one filter holder with the at least one observation filter of the filter set.

According to a further embodiment a medical optical system for observing fluorescent radiation in biological tissue comprises an illumination system having a light source and illumination optics, to illuminate the tissue with illumination radiation, the medical optical system further comprising an imaging system having imaging optics, to guide radiation emanating from the tissue to an image plane. Thereby, the light source of the illumination system provides light exclusively out of the first wavelength transmission range of the previously described filter set. By using such a light source for example an optimal adaptation to excitation bands of a fluorescent dye is possible. Therein, the light source may, for example, be a laser or a light emitting diode. The imaging system then comprises at least one filter holder with the at least one observation filter of the previously described filter set.

According to an embodiment, the illumination system of the system may further comprise a second light source, wherein the central 90% of the intensity of the radiation emitted by the second light source are caused by radiation of a wavelength range whose longest wavelength is at least 30 nm and in particular at least 45 nm and in particular at least 65 nm and further in particular at least 80 nm shorter compared to the shortest wavelength of the second wavelength transmission range of the at least one observation filter. Thereby it may be ensured that radiation transmitted by the second wavelength transmission range and radiation emitted by the second light source have different colors. As second light source a light emitting diode or a laser may be used, for example.

According to an embodiment the first wavelength transmission range may comprise the excitation band of a used fluorescent dye or of tissue and the second wavelength transmission range may comprise the fluorescent band of the fluorescent dye or of the tissue.

It is emphasized that a filter set complying with the definition given in the above second and third alternative embodiments of the filter set may additionally comply with the definition given in the above first embodiment of the filter set.

Further embodiments are directed to observing the fluorescent radiation and observing the adjacent tissue substantially simultaneously. The term "substantially simultaneously" is understood in the way that the observing occurs synchronously or sequentially, wherein for sequential observing a temporal interval between observing the fluorescent radiation and observing the adjacent tissue amounts to less than 0.5 seconds and in particular less than 0.25 seconds.

Finally, a method of selecting filters of a filter set adapted for observing fluorescent radiation in biological tissue comprises the steps of selecting at least one illumination filter having the properties of the illumination filter of one of the above described filter sets and the step of selecting at least one observation filter having the properties of the observation filter of the same filter set as the filter set that was used for defining the properties of the at least one illumination filter.

A filter set for observing fluorescent radiation in biological tissue having at least one illumination filter (L; L') and having at least one observation filter (O1, O1'; O2, O2') is proposed. The at least one illumination filter (L; L') is arrangeable in an illumination system of an optical system and has a first wavelength transmission range (D1) and a first wavelength blocking range (S1) comprising wavelengths ($\lambda$) longer than those comprised in the first wavelength transmission range (D1). The at least one observation filter (O1, O1'; O2, O2') is arrangeable in an imaging system of the optical system and has a second wavelength transmission range (D2) comprising wavelengths ($\lambda$) longer than those comprised in the first wavelength transmission range (D1) of the at least one illumination filter (L; L'), and has a second wavelength blocking range (S2, S2') comprising wavelength ($\lambda$) shorter than those comprised in the second wavelength transmission range (D2). Thereby the transmittance ($T_L(\lambda)$, $T_L(\lambda)$, $T_{O1}(\lambda)$, $T_{O2}(\lambda)$) for wavelengths ($\lambda$) both in the first wavelength transmission range (D1) and the second wavelength transmission range (D2) is greater than 0.5 and is smaller than 0.5 in both the first wavelength blocking range (S1) and in the second wavelength blocking range (S2, S2'). Further, a product of the transmittance ($T_L(\lambda)$, $T_L(\lambda)$) for wavelengths ($\lambda$) of the at least one illumination filter (L; L') and the transmittance ($T_{O1}(\lambda)$, $T_{O2}(\lambda)$) for wavelength ($\lambda$) of the at least one observation filter (O1, O1'; O2, O2') both in the second wavelength transmission range (D2) and in the second wavelength blocking range (S2, S2') is smaller than 0.05. For wavelengths ($\lambda$) shorter than those comprised in the second wavelength blocking range (S2, S2') the at least one observation filter (O1, O1'; O2, O2') further has a third wavelength transmission range (D3, D3'). The first, the second, and the third wavelength transmission ranges (D1, D2, D3, D3') and the first and the second wavelength blocking ranges (S1, S2, S2') at least partially comprise the spectral range from 350 nm to 780 nm. Further, the at least one illumination filter (L; L') and the at least one observation filter (O1, O1'; O2, O2') satisfy the dimensioning rule $$X < \int_{350}^{Z} T_L(\lambda) \cdot T_O(\lambda) d\lambda < Y.$$

Thereby, $T_L(\lambda)$ is the transmittance for wavelengths $\lambda$ of the at least one illumination filter (L; L'), $T_O(\lambda)$ is the transmittance for wavelengths $\lambda$ of the at least one observation filter (O1, O1'; O2, O2'), $X \geq 0.02$ nm, $Y \leq 5$ nm, and Z is a wavelength between 480 nm and 595 nm.

BRIEF DESCRIPTION OF THE DRAWINGS

The foregoing as well as other advantageous features of the Embodiments are explained in more detail with reference to drawings. Thereby, the same or similar reference signs are used, as far as possible, to refer to the same or similar elements. It is noted that not all possible embodiments of the present invention necessarily exhibit each and every, or any, of the advantages identified herein.

DETAILED DESCRIPTION OF THE INVENTION

The embodiments of the filter set are explained in the following using the medical optical system shown in FIG. 4 as an example.

Figure 4:
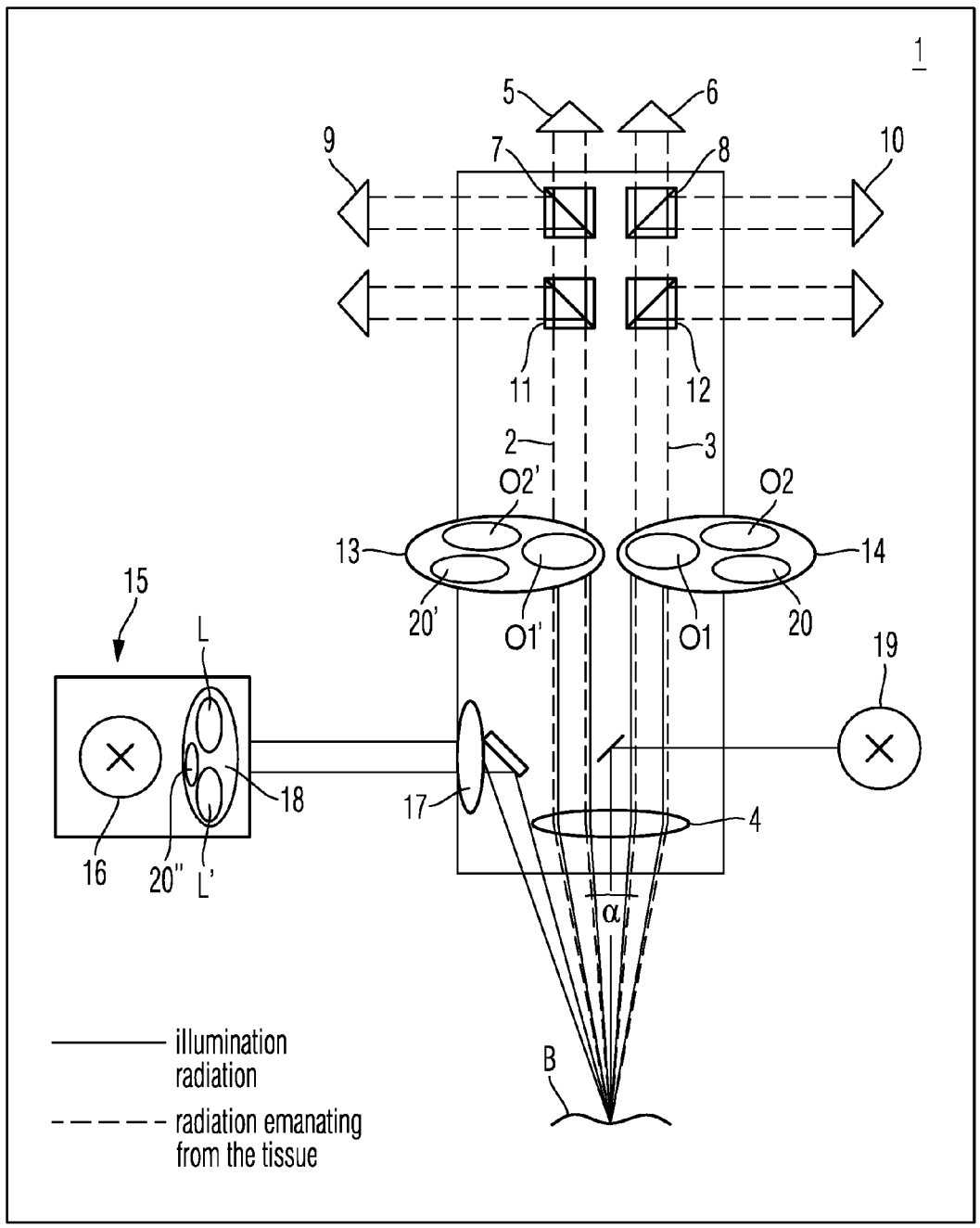
FIG. 4 schematically shows a medical optical system in which the filter set according to the first and the second embodiments is employed.

The system 1 shown in FIG. 4 is a surgical microscope with two stereoscopic left and right beam paths 2, 3 whose central beams (not shown) meet at an observed biological tissue B including a stereo angle α of between 6° and 12°. Using the two stereoscopic left and right beam paths 2, 3 simultaneously observing the observed biological tissue B is possible.

For establishing the two stereoscopic beam paths 2, 3 an imaging optics 4 is provided that is only schematically shown in FIG. 4. The imaging optics 4 comprises plural (not shown) optical lenses and allows an adjustment of the working distance as well as an adjustment of the imaging magnification of the system 1.

Using the two stereoscopic beam paths 2, 3 radiation emanating from the tissue B is guided by the imaging optics 4 and by using oculars 5, 6 to an image plane (not shown) which lies in the eye of a user. In this way the tissue B is imaged to the image plane. Further, the radiation is passed to an infrared camera 9 as well as to a normal camera 10 via semi-transparent mirrors 7, 8. Further, the radiation is passed to auxiliary observer beam paths via semi transparent mirrors 11, 12.

The system 1 further comprises two filter wheels 13, 14, to selectively arrange first and second observation filters O1, O1', O2, O2' or an opening 20, 20' in one of the two stereoscopic beam paths 2, 3. For a motor driven actuation of the filter wheels 13, 14 a not especially shown controller is provided.

To illuminate the tissue B with illumination radiation the system further comprises an illumination system 15 having a light source 16 in the form of a xenon light source and having illumination optics 17. Therein, a further filter wheel 18 is arranged between the light source 16 and the illumination optics 17, which filter wheel 18 carries the first and the second illumination filters L, L'. The filter wheel 18 further comprises a combined UV-IR-blocking filter 20". The combined UV-IR-blocking filter 20" has, in the present embodiment, a transmittance of below 0.2 and in particular below 0.05 for wavelengths smaller than 400 nm and for wavelengths longer than 700 nm, and has a transmittance of above 0.8 and in particular above 0.95 for wavelengths between 410 nm and 690 nm. Thus, the combined UV-IR-blocking filter 20" is well adapted for the usage of the xenon light source 16 for illumination of the observed biological tissue B. However, the combined UV-IR-blocking filter 20" is not necessarily arranged at the filter wheel 18, but may alternatively also be arranged at another location in the illumination beam path. In this case the filter wheel has, instead of the combined UV-IR-blocking filter, an opening and the combined UV-IR-blocking filter 20" arranged at another location in the illumination beam path is preferably switchable, i.e. optionally arrangeable in and removable from the illumination beam path.

The first and the second observation filters O1, O1', O2, O2' and the first and the second illumination filters L, L' pairwise form first and second filter sets. Thereby, the illumination filters L, L' and the observation filters O1, O1', O2, O2' of each filter set are arranged in series related to radiation emitted from the light source and reflected at the tissue B.

Figure 1:
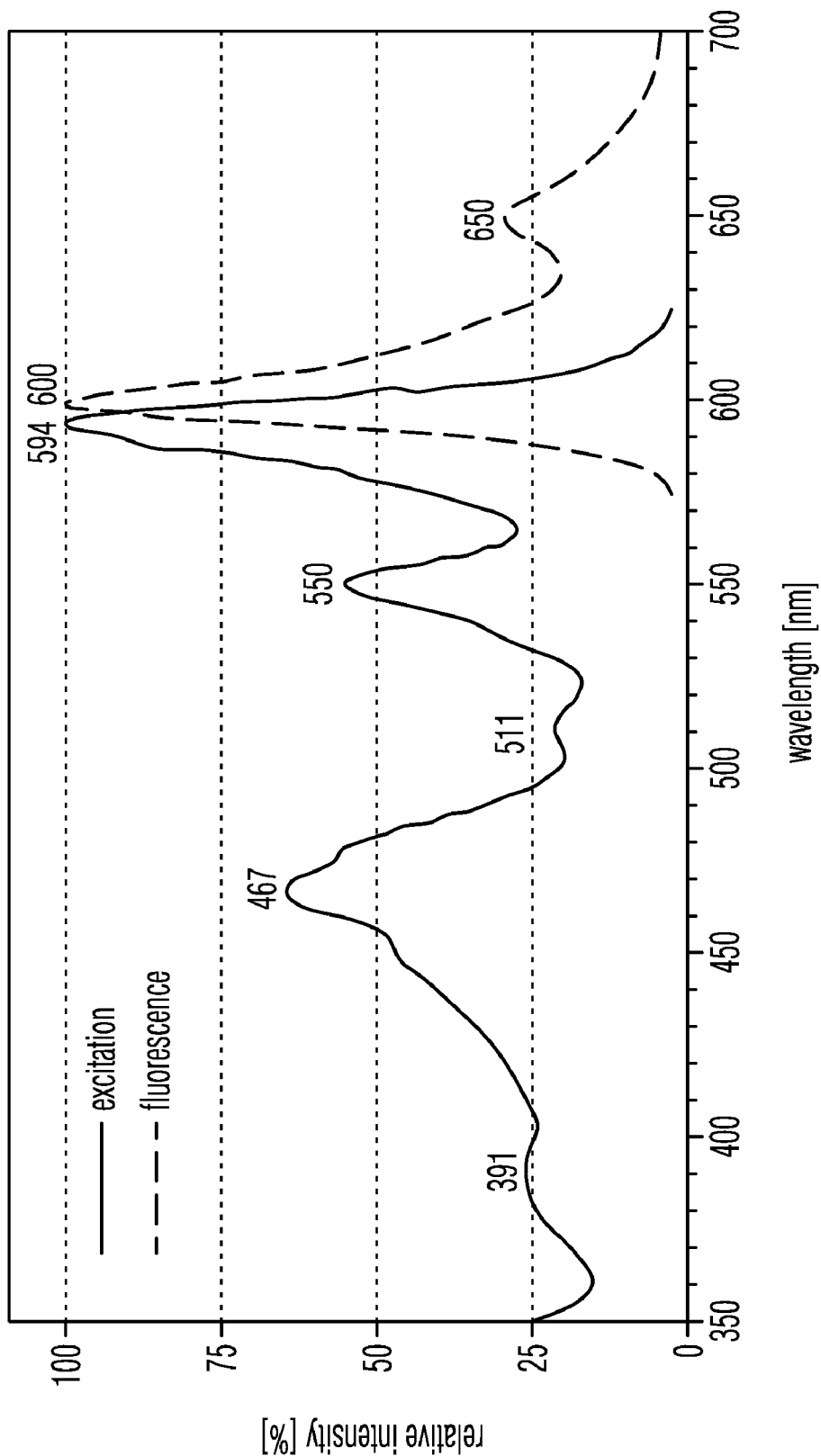
FIG. 1 schematically shows the excitation bands and fluorescent bands of Hypericin.
Figure 2A:
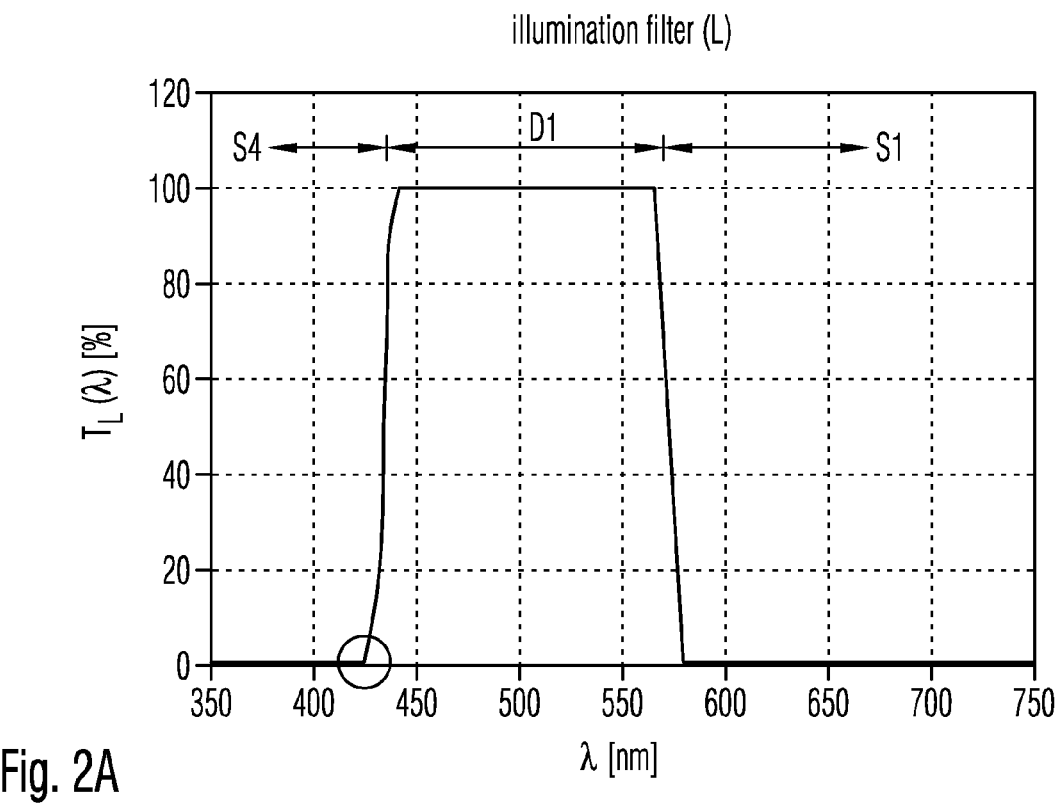
FIG. 2A shows the transmittance for wavelengths of an illumination filter of a filter set according to a first embodiment.
Figure 3A:
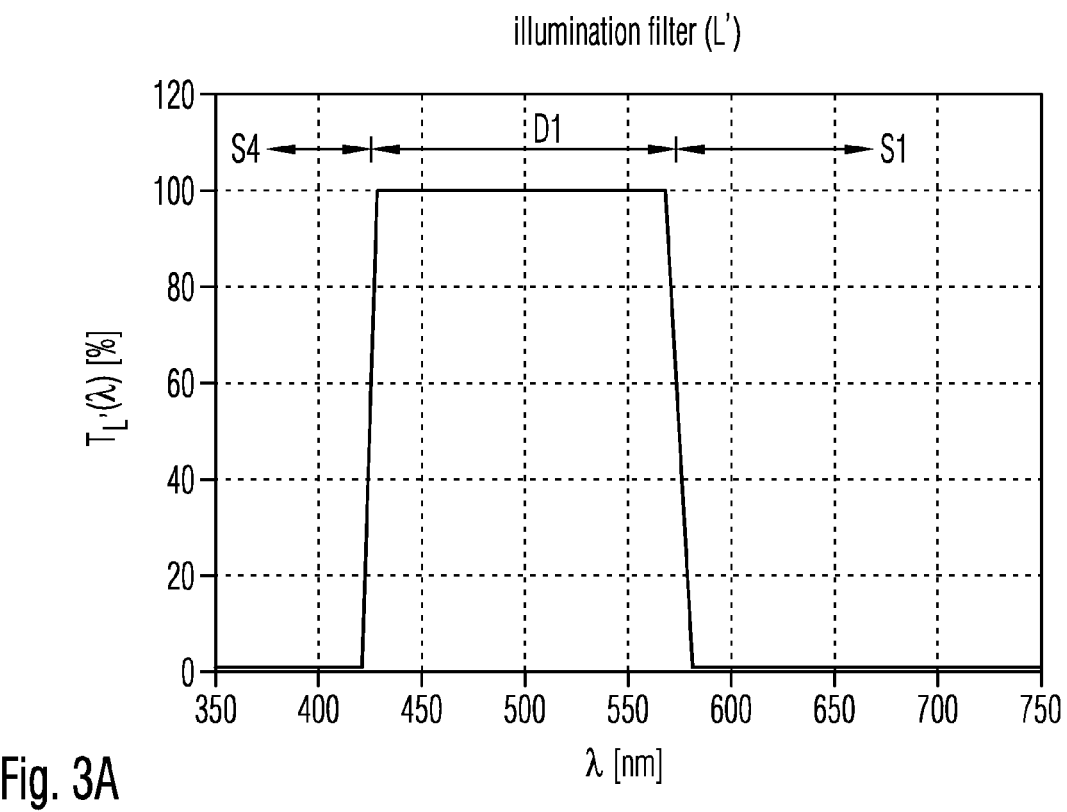
FIG. 3A shows the transmittance for wavelengths of an illumination filter of a filter set according to a second embodiment.

As is shown in FIGS. 2A and 3A, the illumination filter L, L' has a first wavelength transmission range D1 for radiation emitted by the light source 16 with wavelengths λ between 435 nm and 570 nm, wherein a transmittance $T_L(\lambda)$, $T_{L'}(\lambda)$ for these wavelengths λ is greater than 0.95. Further, the illumination filter L, L' has a first wavelength blocking range S1 for wavelengths (λ) longer than 570 nm, where a transmittance $T_L(\lambda)$, $T_{L'}(\lambda)$ for these wavelengths λ is smaller than 0.01. Moreover, the illumination filter L, L' has a fourth wavelength blocking range S4 for wavelengths λ smaller than 435 nm, where a transmittance $T_L(\lambda)$, $T_{L'}(\lambda)$ for these wavelengths (λ) is smaller than 0.01. Consequently, the illumination filter L, L' transmits light originating from the light source 16 with a broad spectrum from 435 nm to 570 nm. This broad spectrum comprises two excitation maxima of the fluorescent dye Hypericin at 467 nm and 550 nm. However, an excitation of the excitation maximum of the fluorescent dye Hypericin at 594 nm is not possible with the illumination filters L, L'.

The two first and second illumination filters L, L' in particular differ in that for the first illumination filter L the flank at 435 nm in the transition range between the first wavelength transmission range D1 and the fourth wavelength blocking range S4 runs in a bent way, whereas for the second illumination filter L' the transitions are sharply formed.

An illumination filter L' having the transmittance $T_{L'}(\lambda)$ for wavelengths λ shown in FIG. 3A is purchasable in the year 2008 under the denomination "Brightline HC 460/80" from the company SEMROCK, 3625 Buffalo Road, Suite 6, Rochester, N.Y. 14624, USA. This filter might further be optimised in that also the excitation maximum of the fluorescent dye Hypericin at 594 nm is comprised and in that thus the first wavelength transmission range D1 is extended towards longer wavelengths (for example up to about 595 nm) at the expense of the first wavelength blocking range S1.

An illumination filter L having the transmittance $T_L(\lambda)$ for wavelengths λ shown in FIG. 2A may for example be obtained by modification of the preceding illumination filter L'.

Figure 2B:
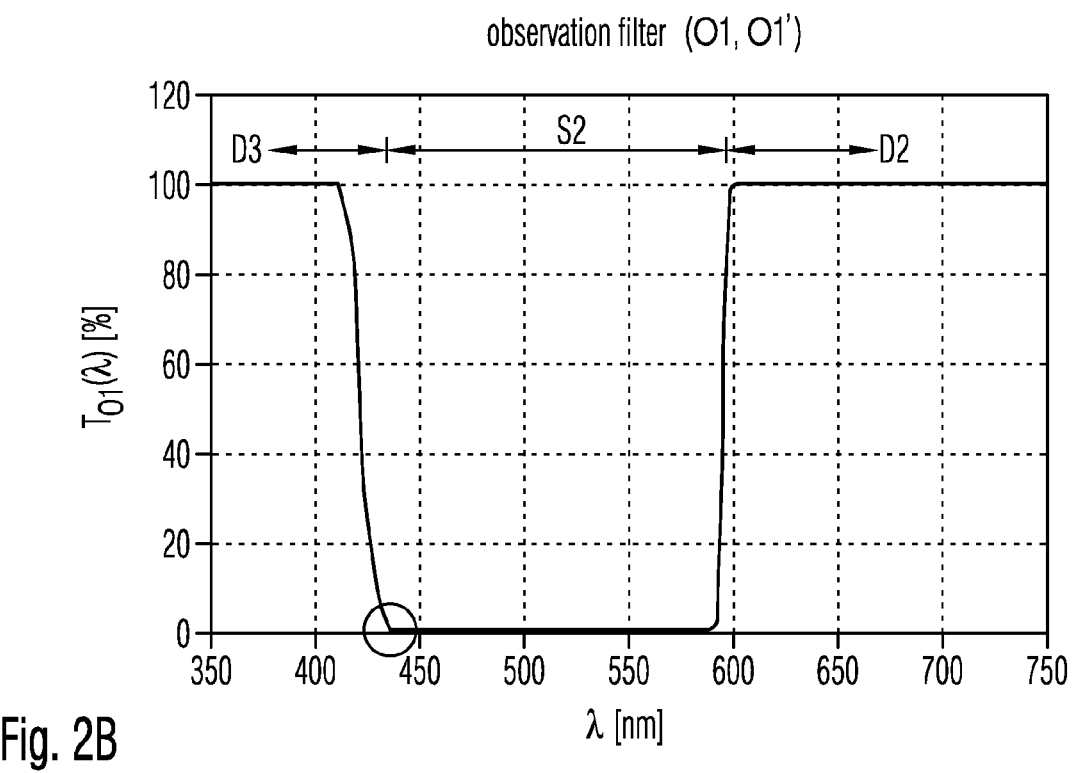
FIG. 2B shows the transmittance for wavelengths of an observation filter of a filter set according to the first embodiment.
Figure 3B:
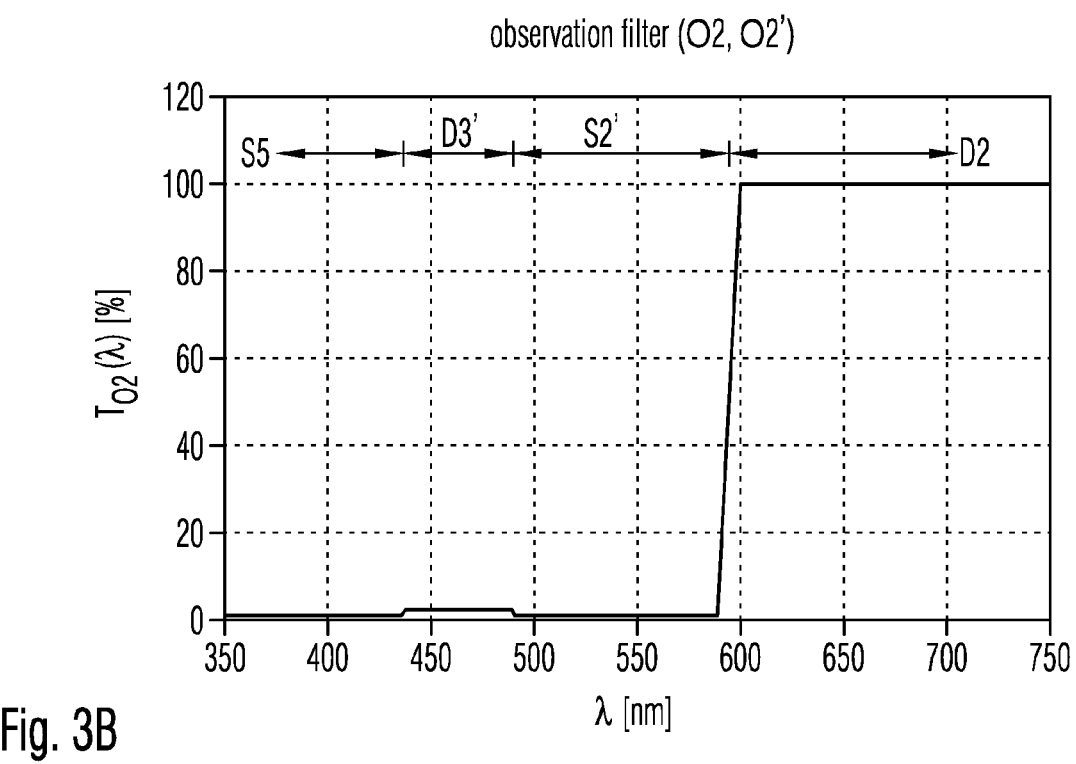
FIG. 3B shows the transmittance for wavelengths of an observation filter of a filter set according to the second embodiment.

As is shown in the FIGS. 2B and 3B, the observation filter O1, O1', O2, O2' has for wavelengths λ longer than 590 nm a second wavelength transmission range D2 where a transmittance $T_{O1}(\lambda)$, $T_{O2}(\lambda)$ for these wavelengths λ is greater than 0.95.

The second wavelength transmission range D2 thus comprises two fluorescence maxima of the fluorescent dye Hypericin at 600 nm and 650 nm.

For wavelengths λ shorter than 590 nm the observation filter O1, O1', O2, O2' has a second wavelength blocking range S2, S2', where a transmittance $T_{O1}(\lambda)$, $T_{O2}(\lambda)$ for these wavelengths λ is smaller than 0.01.

A product of the transmittance $T_L(\lambda)$, $T_{L'}(\lambda)$ for wavelengths λ of the illumination filters L, L' and the transmittance $T_{O1}(\lambda)$, $T_{O2}(\lambda)$ for wavelengths λ of the observation filters O1, O1', O2, O2' in the second wavelength transmission range D2 (and thus for wavelengths longer than 590 nm) and in the second wavelength blocking range S2, S2' is smaller than 0.01. Consequently, fluorescent radiation is not superimposed by illumination radiation emitted by the light source 16 so that simultaneously observing fluorescence and adjacent tissue is possible. The fluorescent radiation is radiation caused by fluorescence and may also be called fluorescence radiation.

In the following two different embodiments of the filter set are explained in detail. These embodiments in particular differ in the way in which an accurately defined portion of the spectrum emitted by the light source 16 successively passes the illumination filter L, L' as well as also the observation filter O1, O1', O2, O2', to enable, in addition to observing fluorescence, observing non-fluorescent tissue. In both embodiments the observation filters O1, O1', O2, O2' have, starting from the second wavelength blocking range S2, S2' towards shorter wavelengths, a third wavelength transmission range D3, D3'. This range is spaced apart from the second wavelength transmission range D2 by an amount corresponding to the second wavelength blocking range S2, S2' so that the radiation transmitted in the second and the third wavelength transmission ranges D2, D3, D3' has significantly different wavelengths and thus different colours. Further, the transmittance for wavelengths of the observation filter O1, O1', O2, O2' has in both embodiments a local minimum which is located between the second and the third wavelength transmission ranges D2, D3, D3' (which respectively form local maxima of the transmittance for wavelengths).

In the following a first embodiment of the filter set is explained in detail referring to FIGS. 2A to 2D. In this first embodiment the afore described first illumination filter L is used.

For the first embodiment the observation filter O1, O1' further has, for wavelengths λ shorter than 425 nm and thus for wavelengths λ shorter than those comprised in the second wavelength blocking range S2, a third wavelength transmission range D3 in which a transmittance $T_{O1}(\lambda)$ for these wavelengths is greater than 0.95. This range is open towards shorter wavelengths λ. The second and the third wavelength transmission ranges D2, D3 are spaced apart from each other by a spectral width of 165 nm so that the second wavelength blocking range S2 has a spectral width of 165 nm.

Figure 2C:
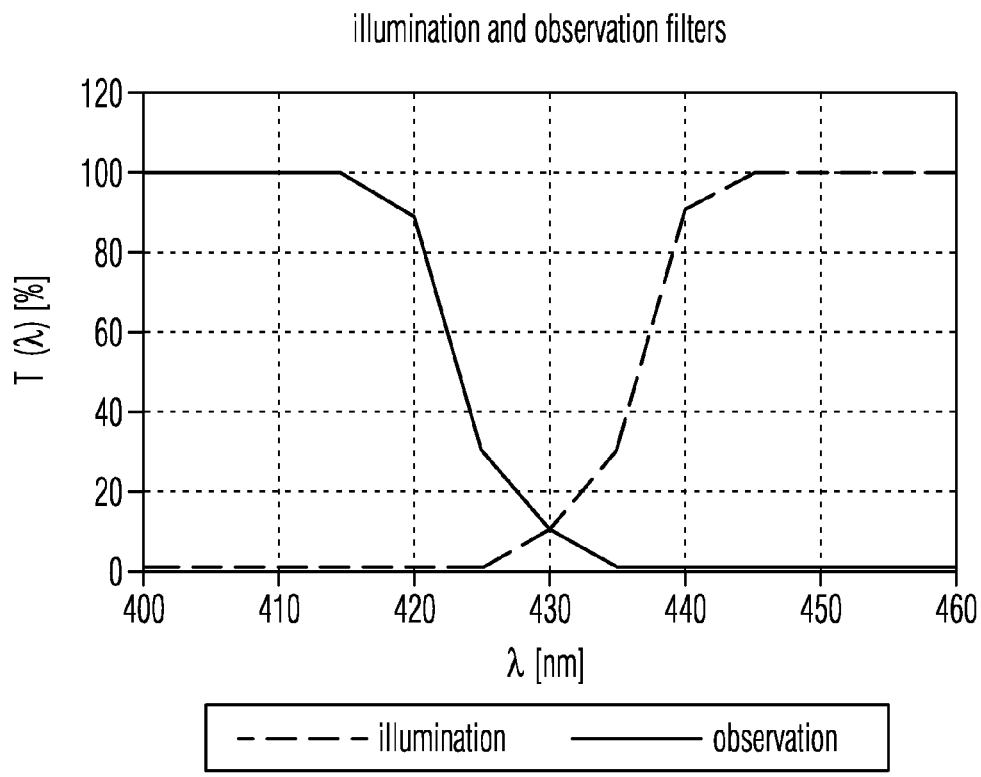
FIG. 2C shows in a magnified way an overlap range of the transmittances for wavelengths of the illumination filter and the observation filter of the filter set according to the first embodiment.

In the vicinity of the wavelength 430 nm an overlap between the first wavelength transmission range D1 of the illumination filter L and the third wavelength transmission range D3 of the observation filter O1, O1' occurs. This is facilitated in that also for the first observation filter O1, O1' the flank at 425 nm in the transition region between the second wavelength blocking range S2 and the third wavelength transmission range D2 is not sharply formed but runs in a bent way. This overlap is shown in FIG. 2C in a magnified way.

Figure 2D:
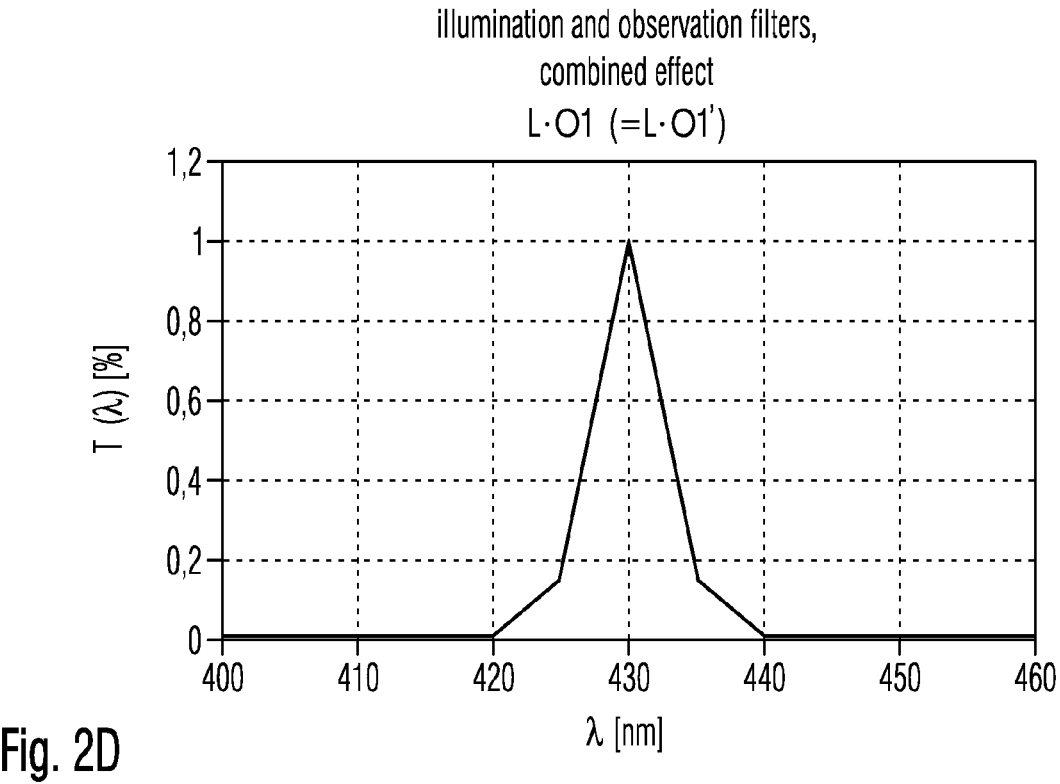
FIG. 2D shows the product of the transmittances for wavelengths of the illumination filter and the observation filter of the filter set according to the first embodiment in the overlap range.

Within a spectral band between about 425 nm and 435 nm a product of the transmittance $T_L(\lambda)$ for wavelengths λ of the illumination filter L with the transmittance $T_{O1}(\lambda)$ for wavelengths λ of the observation filter O1, O1' is greater than 0.004 and is smaller than 0.004 outside of this range in the third wavelength transmission range D3 (and thus towards shorter wavelengths). The maximum of this product for a wavelength λ of 430 nm lies at 0.01. This is shown in FIG. 2D.

The first embodiment is thus based on a purposeful overlap of flanks of the transmittances $T_L(\lambda)$, $T_{O1}(\lambda)$ for wavelengths λ of the illumination filter L and the observation filter O1, O1'.

Figure 3C:
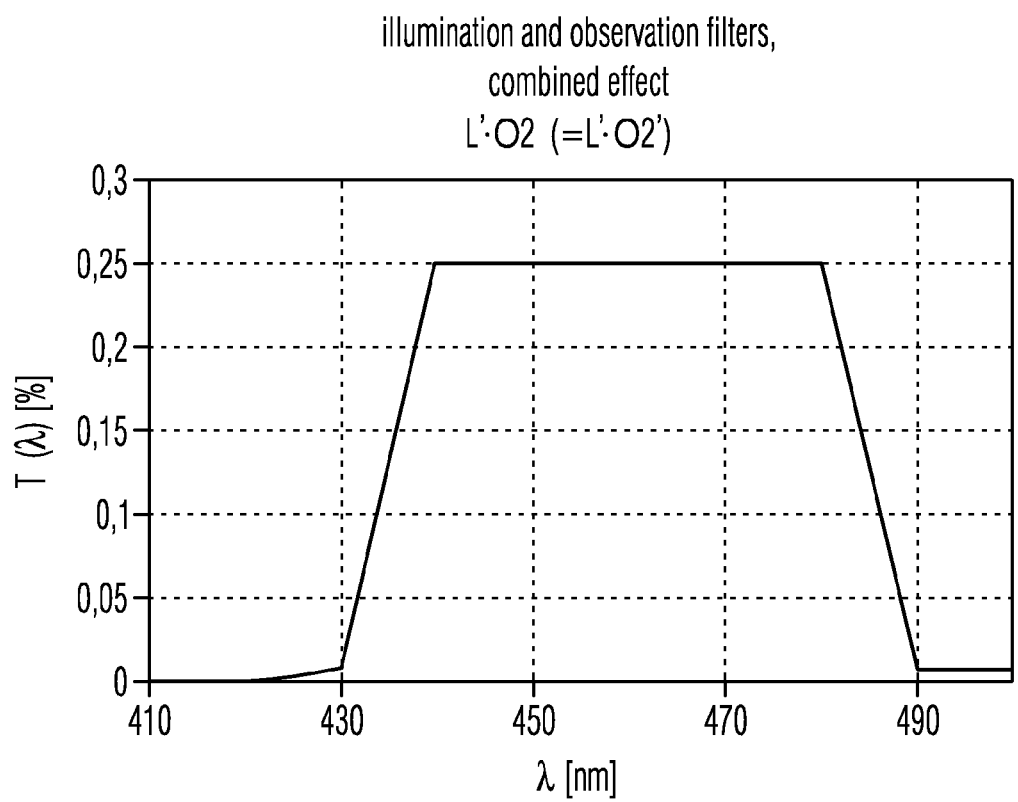
FIG. 3C shows the product of the transmittances for wavelengths of the illumination filter and the observation filter of the filter set according to the second embodiment in an overlap range.

In the following a second embodiment of the filter set is explained in detail referring to FIGS. 3A to 3C. In this second embodiment the afore described second illumination filter L' is used.

Also in this embodiment the observation filter O2, O2' further has a third wavelength transmission range D3' comprising wavelengths λ shorter than 485 nm and thus for wavelengths λ shorter than those comprised in the second wavelength blocking range S2'. The transmittance $T_{O2}(\lambda)$ for wavelengths λ of the observation filter O2, O2' in the third wavelength transmission range D3' in a spectral band between 435 nm and 485 nm thereby is greater than 0.001 and is smaller than 0.001 in the second wavelength blocking range D2' and thus between 485 nm and about 580 nm. Thus, the second wavelength blocking range S2' has a spectral width of about 95 nm. Further, the transmittance $T_{O2}(\lambda)$ for wavelengths λ of the observation filter O2, O2' for wavelengths λ shorter than the third wavelength transmission range D3' and thus shorter than 435 nm in a fifth wavelength blocking range S5 is smaller than 0.001.

As is evident from a comparison of FIGS. 3A and 3B, the third wavelength transmission range D3' of the observation filter O2, O2' entirely lies within the first wavelength transmission range D1 of the illumination filter L'. Consequently, the requirements regarding the accuracy of the spectral position of the third wavelength transmission range D3' are lower for the second embodiment than for the first embodiment.

However, it is not necessary that the third wavelength transmission range D3' of the observation filter O2, O2' entirely lies within the first wavelength transmission range D1 of the illumination filter L'. A partial overlap can be sufficient.

The transmittance $T_{O2}(\lambda)$ for wavelengths λ of the observation filter O2, O2' in the third wavelength transmission range D3' may be significantly lower than in the first embodiment, since the second illumination filter L' has its maximal transmittance $T_L(\lambda)$ for wavelengths λ in the third wavelength transmission range D3'. Instead the spectral width of the third wavelength transmission range D3' is larger in the second embodiment than in the first embodiment. Thereby, the illumination of non-fluorescent tissue occurs with larger spectral width in the second embodiment than in the first embodiment. Consequently, the information content and the recognizability of non-fluorescent tissue is enhanced compared to the first embodiment.

Within the spectral band from 435 nm to 485 nm a product of the transmittance $T_L(\lambda)$ for wavelengths λ of the illumination filter L' and the transmittance $T_{O2}(\lambda)$ for wavelengths λ of the observation filter O2, O2' is greater than 0.001 and is smaller than 0.001 outside of this spectral band in the third wavelength transmission range D3'. Hereby, this product has a maximum of 0.0025 in a spectral band from about 440 nm to 480 nm.

Thus, the second embodiment is based on a purposefully spectrally broad superposition of the first wavelength transmission range D1 of the illumination filter L' and the third wavelength transmission range D3' of the observation filter O2, O2'.

An observation filter O2, O2' having the transmittance $T_{O2}(\lambda)$ for wavelengths λ shown in FIG. 3B is purchasable in the year 2008 under the denomination "Brightline HC 620/52" from the company SEMROCK, 3625 Buffalo Road, Suite 6, Rochester, N.Y. 14624, USA.

In both preceding embodiments a product of the transmittance $T_L(\lambda)$, $T_L(\lambda)$ for wavelengths λ of the respective illumination filter L, L' with the transmittance $T_{O1}(\lambda)$, $T_{O2}(\lambda)$ for wavelengths λ of the respective observation filter O1, O1', O2, O2' in a spectral range between the first wavelength transmission range D1 and the second wavelength transmission range D2 of more than 5 nm of spectral width is always smaller than 0.01 and in particular always smaller than 0.001.

Further, it holds for both embodiments that the illumination filter L, L' and the at least one observation filter O1, O1', O2, O2' satisfy the following relations:

$$X < \int_{350}^{Z} T_L(\lambda) \cdot T_O(\lambda) d\lambda < Y.$$

Thereby $T_L(\lambda)$ is the transmittance for wavelengths λ of the illumination filter L, L'; $T_O(\lambda)$ is the transmittance of wavelengths λ of the observation filter O1, O1', O2, O2'; X≧0.05 nm; Y≦1.5 nm; and 480 nm≦Z≦580 nm.

Even though the previously described filter sets each comprise exactly one illumination filter and exactly one observation filter (per observation beam path) having the desired properties, the desired filter properties may optionally also be achieved by simultaneous provision of more than one illumination filter or more than one observation filter in series. Further, the preceding parameters of the embodiments are merely exemplary and do not restrict the ranges given in the introduction of the description and in the claims. Also, the use of Hypericin as fluorescent dye is only optional.

The used filters may for example be transmission filters or reflection filters. Also mixing or combining these both filter types is possible. Further, for example between the observed tissue and the illumination system additional filters, such as for example at least one of UV-blocking filters for filtering UV-light having a wavelength smaller than 400 nm and IR-blocking filters for filtering radiation having a wavelength longer than 700 nm, may be provided. These additional filters serve for protecting the treated patient and the treating physician. It is emphasised that all filters described in the present application may be one single filter or may be composed of a combination of plural consecutive filters.

According to an alternative embodiment additionally to the broad-band light source 16 of the illumination system 15 of the optical system a second light source 19 is provided which provides light exclusively from the afore described first wavelength transmission range D1 and which in particular provides light of the excitation maxima of the fluorescent dye Hypericin. In the embodiment shown in FIG. 4 this second light source 19 is realised by light emitting diodes. An advantage of such a second light source is that the brightness of the light source and thus of the excitation of the fluorescence is freely controllable without deteriorating the illumination of non-fluorescent tissue portions.

According to a further alternative embodiment instead of simultaneous observing fluorescent radiation and non-fluorescent tissue observing is provided. In this case the emission of excitation radiation in the first wavelength transmission range D1 may be performed in a pulsed way to a continuous emission of broad band white light using the first light source 16.

In the context of this application the spectral width of a wavelength range defined by means of its transmittance is measured between those wavelengths for which a threshold of the transmittance indicative of the respective range is exceeded or undercut. If for example the first and the second wavelength transmission range is denoted as the range in which the transmittance of the wavelengths is greater than 0.5, the width of the range is measured starting from the shortest wavelength for which the transmittance exceeds 0.5 for the first time towards longer wavelengths up to that wavelength for which the transmittance undercuts 0.5 for the first time. In the same way a spectral distance between two different wavelength ranges may be measured using the thresholds for the transmittance defining the respective wavelength ranges.

Moreover, in the context of the present application "filter arrangeable in an optical system" means that the filter is adapted to be arranged in an optical path of the system.

A method of selecting a filter set adapted for observing fluorescent radiation in biological tissue comprises the following steps: selecting at least one illumination filter having the transmittance for wavelengths of the illumination filter of one of the above described filter sets; and selecting at least one observation filter having the transmittance for wavelengths of the observation filter of the same filter set as the filter set that was used for defining the properties of the at least one illumination filter. These steps can be performed in any order.

What is claimed is:

1. A filter set for observing fluorescent radiation in biological tissue, the filter set comprising:
   at least one illumination filter arrangeable in an illumination system of an optical system and having a first wavelength transmission range and a first wavelength blocking range, the first wavelength blocking range comprising wavelengths longer than those comprised in the first wavelength transmission range; and
   at least one observation filter arrangeable in an imaging system of the optical system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
   wherein a transmittance for wavelengths in the first wavelength transmission range and the second wavelength transmission range is greater than 0.5, and a transmittance for wavelengths in the first wavelength blocking range and the second wavelength blocking range is smaller than 0.5;
   wherein a product of the transmittance for wavelengths of the at least one illumination filter and the transmittance for wavelengths of the at least one observation filter in the second wavelength transmission range and the second wavelength blocking range is smaller than 0.05;
   wherein the at least one observation filter has a third wavelength transmission range comprising wavelengths shorter than those comprised in the second wavelength blocking range;
   wherein the first, the second and the third wavelength transmission ranges as well as the first and the second wavelength blocking ranges each at least partially comprise the spectral range from 350 nm to 780 nm; and
   wherein the at least one illumination filter and the at least one observation filter satisfy the following dimensioning rule:

$$X < \int_{350}^{Z} T_L(\lambda) \cdot T_O(\lambda) d\lambda < Y, \text{ wherein}$$

$T_L(\lambda)$ is the transmittance for wavelengths $\lambda$ of the at least one illumination filter;
   $T_O(\lambda)$ is the transmittance for wavelengths $\lambda$ of the at least one observation filter;
   $X \geq 0.02$ nm;
   $Y \leq 5$ nm; and
   480 nm $\leq Z \leq$ 595 nm.

2. The filter set according to claim 1, wherein $X \geq 0.04$ nm, $Y \leq 3$ nm, and 500 nm $\leq Z \leq$ 595 nm.

3. The filter set according to claim 1, wherein a product of the transmittance for wavelengths of the at least one illumination filter and the transmittance for wavelengths of the at least one observation filter in the third wavelength transmission range within a predetermined spectral band of less than 60 nm is greater than 0.004 and is smaller than 0.004 outside of this spectral band.

4. The filter set according to claim 1, wherein the transmittance for wavelengths of the at least one observation filter in the third wavelength transmission range for ranges of wavelengths from 350 nm to 590 nm is greater than 0.001 and is smaller than 0.001 outside of these ranges.

5. The filter set according to claim 1, wherein the second wavelength blocking range has a spectral width of at least 45 nm.

6. The filter set according to claim 1, wherein a product of the transmittance for wavelengths of the at least one illumination filter and the transmittance for wavelengths of the at least one observation filter in a spectral range between the first wavelength transmission range and the second wavelength transmission range of at least 3 nm of spectral width is smaller than 0.05.

7. The filter set according to claim 1, wherein a product of the transmittance for wavelengths of the at least one illumination filter and the transmittance for wavelengths of the at least one observation filter both in the second wavelength transmission range and the second wavelength blocking range is smaller than 0.01.

8. The filter set according claim 1, wherein the transmittance for wavelengths of the at least one illumination filter in the first wavelength transmission range for ranges of wavelengths from 415 nm to 595 nm is greater than 0.5 and is smaller than 0.5 outside of these ranges.

9. The filter set according to claim 1, wherein the transmittance for wavelengths of the at least one observation filter in the second wavelength transmission range for wavelengths longer than 585 nm is greater than 0.5 and is smaller than 0.5 for shorter wavelengths.

10. The filter set according to claim 1, wherein at least one of the following holds:
the transmittance for wavelengths of the at least one illumination filter in the first wavelength transmission range is greater than 0.9;
the transmittance for wavelengths of the at least one observation filter in the second wavelength transmission range is greater than 0.9.

11. The filter set according to claim 1, wherein the transmittance for wavelengths of the at least one observation filter in the third wavelength transmission range for wavelengths smaller than 450 nm is greater than 0.01 and is smaller than 0.01 for longer wavelengths.

12. The filter set according to claim 1, wherein a product of the transmittance for wavelengths of the at least one illumination filter and the transmittance for wavelengths of the at least one observation filter in the third wavelength transmission range within a predetermined spectral band of at least 20 nm is greater than 0.001 and is smaller than 0.001 outside of this spectral band.

13. The filter set according to claim 1, wherein the transmittance for wavelengths of the at least one observation filter in the second wavelength blocking range is smaller than 0.001.

14. A filter set for observing fluorescent radiation in biological tissue, the filter set comprising:
at least one illumination filter arrangeable in an illumination system of an optical system and having a first wavelength transmission range and a first wavelength blocking range comprising wavelengths longer than those comprised in the first wavelength transmission range; and
at least one observation filter arrangeable in an imaging system of the optical system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
wherein a transmittance for wavelengths in the first wavelength transmission range and the second wavelength transmission range is greater than 0.5;
wherein a transmittance for wavelengths in the first wavelength blocking range and the second wavelength blocking range is smaller than 0.5;
wherein a product of the transmittance for wavelengths of the at least one illumination filter and the transmittance for wavelengths of the at least one observation filter in the second wavelength transmission range and in the second wavelength blocking range is smaller than 0.05;
wherein the at least one observation filter has a third wavelength transmission range comprising wavelengths shorter than those comprised in the second wavelength blocking range;
wherein the transmittance for wavelengths of the at least one observation filter is greater than 0.01 in the third wavelength transmission range and is smaller than 0.01 in the second wavelength blocking range;
wherein the second wavelength blocking range has a spectral width of at least 100 nm; and
wherein the first, the second, and the third wavelength transmission ranges and the first and the second wavelength blocking range at least partially comprise the spectral range from 350 nm to 780 nm.

15. The filter set according to claim 14, wherein a product of the transmittance for wavelengths of the at least one illumination filter and the transmittance for wavelengths of the at least one observation filter in the third wavelength transmission range within a predetermined spectral band of less than 60 nm is greater than 0.004 and is smaller than 0.004 outside of this spectral band.

16. The spectral set according to claim 15, wherein the product of the transmittance for wavelengths of the at least one illumination filter and the transmittance for wavelengths of the at least one observation filter has within the predetermined spectral band a maximum greater than 0.005.

17. The filter set according to claim 14, wherein a product of the transmittance for wavelengths of the at least one illumination filter and the transmittance for wavelengths of the at least one observation filter within a predetermined spectral band from 400 nm to 460 nm is greater than 0.004 and is smaller than 0.004 outside of this spectral band.

18. The filter set according to claim 17, wherein the product of the transmittance for wavelengths of the at least one illumination filter and the transmittance for wavelengths of the at least one observation filter within the predetermined spectral band from 400 nm to 460 nm is greater than 0.004 and less than 0.05.

19. The filter set according to claim 14, wherein the transmittance for wavelengths of the at least one observation filter in the third wavelength transmission range for wavelengths smaller than 450 nm is greater than 0.01 and is smaller than 0.01 for longer wavelengths.

20. The filter set according to claim 19, wherein the transmittance for wavelengths of the at least one observation filter in the third wavelength transmission range for wavelengths smaller than 450 nm is greater than 0.5 and is smaller than 0.01 for longer wavelengths.

21. The filter set according to claim 14, wherein the transmittance for wavelengths of the at least one observation filter in the third wavelength transmission range for ranges of wavelengths from 350 nm to 590 nm is greater than 0.001 and is smaller than 0.001 outside of these ranges.

22. The filter set according to claim 14, wherein the second wavelength blocking range has a spectral width of at least 45 nm.

23. The filter set according to claim 14, wherein the transmittance for wavelengths of the at least one observation filter is in the second wavelength blocking range smaller than 0.001.

24. The filter set according to claim 14, wherein a product of the transmittance for wavelengths of the at least one illumination filter and the transmittance for wavelengths of the at least one observation filter in a spectral range between the first wavelength transmission range and the second wavelength transmission range of at least 3 nm of spectral width is smaller than 0.05.

25. The filter set according to claim 14, wherein a product of the transmittance for wavelengths of the at least one illumination filter and the transmittance for wavelengths of the at least one observation filter both in the second wavelength transmission range and the second wavelength blocking range is smaller than 0.01.

26. The filter set according claim 14, wherein the transmittance for wavelengths of the at least one illumination filter in the first wavelength transmission range for ranges of wavelengths from 415 nm to 595 nm is greater than 0.5 and is smaller than 0.5 outside of these ranges.

27. The filter set according to claim 14, wherein the transmittance for wavelengths of the at least one observation filter in the second wavelength transmission range for wavelengths longer than 585 nm is greater than 0.5 and is smaller than 0.5 for shorter wavelengths.

28. The filter set according to claim 14, wherein at least one of the following holds:
the transmittance for wavelengths of the at least one illumination filter in the first wavelength transmission range is greater than 0.9;
the transmittance for wavelengths of the at least one observation filter in the second wavelength transmission range is greater than 0.9.

29. A filter set for observing fluorescent radiation in biological tissue, the filter set comprising:
at least one illumination filter arrangeable in an illumination system of an optical system and having a first wavelength transmission range and a first wavelength blocking range comprising wavelengths longer than those comprised in the first wavelength transmission range; and
at least one observation filter arrangeable in an imaging system of the optical system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
wherein a transmittance for wavelengths in the first wavelength transmission range and the second wavelength transmission range is greater than 0.5 and is, in the first wavelength blocking range and the second wavelength blocking range, smaller than 0.5;
wherein a product of the transmittance for wavelengths of the at least one illumination filter and the transmittance for wavelengths of the at least one observation filter is smaller than 0.05 in the second wavelength transmission range and the second wavelength blocking range;
wherein the at least one observation filter further has a third wavelength transmission range comprising wavelengths shorter than those comprised in the second wavelength blocking range;
wherein the transmittance for wavelengths of the at least one observation filter in the third wavelength transmission range across a spectral width of at least 20 nm is greater than 0.001 and is smaller than 0.001 in the second wavelength blocking range;
wherein the second wavelength blocking range has a spectral width of at least 30 nm; and
wherein the first, the second, and the third wavelength transmission ranges as well as the first and the second wavelength blocking ranges at least partially comprise the spectral range from 350 nm to 780 nm.

30. The filter set according to claim 29, wherein the third wavelength transmission range of the at least one observation filter is entirely comprised within the first wavelength transmission range of the at least one illumination filter.

31. The filter set according to claim 29, wherein a product of the transmittance for wavelengths of the at least one illumination filter and the transmittance for wavelengths of the at least one observation filter in the third wavelength transmission range within a predetermined spectral band of at least 20 nm is greater than 0.001 and is smaller than 0.001 outside of this spectral band.

32. The filter set according to claim 31, wherein the product of the transmittance for wavelengths of the at least one illumination filter and the transmittance for wavelengths of the at least one observation filter has within the third wavelength transmission range and the predetermined spectral band, respectively, a maximum of greater than 0.0015.

33. The filter set according to claim 29, wherein a product of the transmittance for wavelengths of the at least one illumination filter and the transmittance for wavelengths of the at least one observation filter in the third wavelength transmission range within a predetermined spectral band of less than 100 nm is greater than 0.001 and is smaller than 0.001 outside of this spectral band.

34. The filter set according to claim 29, wherein a product of the transmittance for wavelengths of the at least one illumination filter and the transmittance for wavelengths of the at least one observation filter within a predetermined spectral band from 350 nm to 590 nm is greater than 0.001 and is smaller than 0.001 outside of this spectral band.

35. The filter set according to claim 29, wherein the transmittance for wavelengths of the at least one observation filter in the third wavelength transmission range for ranges of wavelengths from 350 nm to 590 nm is greater than 0.001 and is smaller than 0.001 outside of these ranges.

36. The filter set according to claim 29, wherein the second wavelength blocking range has a spectral width of at least 45 nm.

37. The filter set according to claim 29, wherein at least one of the following holds:
the transmittance for wavelengths of the at least one illumination filter in the first wavelength transmission range is greater than 0.9;
the transmittance for wavelengths of the at least one observation filter in the second wavelength transmission range is greater than 0.9.

38. The filter set according to claim 29, wherein the transmittance for wavelengths of the at least one observation filter is in the second wavelength blocking range smaller than 0.001.

39. The filter set according to claim 29, wherein a product of the transmittance for wavelengths of the at least one illumination filter and the transmittance for wavelengths of the at least one observation filter in a spectral range between the first wavelength transmission range and the second wavelength transmission range of at least 3 nm of spectral width is smaller than 0.05.

40. The filter set according to claim 29, wherein a product of the transmittance for wavelengths of the at least one illumination filter and the transmittance for wavelengths of the at least one observation filter both in the second wavelength transmission range and the second wavelength blocking range is smaller than 0.01.

41. The filter set according claim 29, wherein the transmittance for wavelengths of the at least one illumination filter in the first wavelength transmission range for ranges of wavelengths from 415 nm to 595 nm is greater than 0.5 and is smaller than 0.5 outside of these ranges.

42. The filter set according to claim 29, wherein the transmittance for wavelengths of the at least one observation filter in the second wavelength transmission range for wavelengths longer than 585 nm is greater than 0.5 and is smaller than 0.5 for shorter wavelengths.

43. A medical optical system for observing fluorescent radiation in biological tissue, the system comprising:
- an illumination system having a light source and illumination optics, to illuminate the tissue with illumination radiation; and
- an imaging system having imaging optics, to guide radiation emanating from the tissue to an imaging plane;
- wherein the medical optical system further comprises a filter set comprising:
- at least one illumination filter arrangeable in the illumination system and having a first wavelength transmission range and a first wavelength blocking range, the first wavelength blocking range comprising wavelengths longer than those comprised in the first wavelength transmission range; and
- at least one observation filter arrangeable in the imaging system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
- wherein a transmittance for wavelengths in the first wavelength transmission range and the second wavelength transmission range is greater than 0.5, and a transmittance for wavelengths in the first wavelength blocking range and the second wavelength blocking range is smaller than 0.5;
- wherein a product of the transmittance for wavelengths of the at least one illumination filter and the transmittance for wavelengths of the at least one observation filter in the second wavelength transmission range and the second wavelength blocking range is smaller than 0.05;
- wherein the at least one observation filter has a third wavelength transmission range comprising wavelengths shorter than those comprised in the second wavelength blocking range;
- wherein the first, the second and the third wavelength transmission ranges as well as the first and the second wavelength blocking ranges each at least partially comprise the spectral range from 350 nm to 780 nm; and
- wherein the at least one illumination filter and the at least one observation filter satisfy the following dimensioning rule:

$$X < \int_{350}^{Z} T_L(\lambda) \cdot T_O(\lambda) d\lambda < Y, \text{ wherein}$$

$T_L(\lambda)$ is the transmittance for wavelengths $\lambda$ of the at least one illumination filter;
$T_O(\lambda)$ is the transmittance for wavelengths $\lambda$ of the at least one observation filter;
$X \geq 0.02$ nm;
$Y \leq 5$ nm; and
$480$ nm $\leq Z \leq 595$ nm;
- wherein the illumination system comprises at least one filter holder in which the at least one illumination filter of the filter set is mounted; and
- wherein the imaging system comprises at least one filter holder in which the at least one observation filter of the filter set is mounted.

44. The medical optical system according to claim 43,
- wherein the illumination system further comprises a second light source; and
- wherein the central 90% of the intensity of the radiation emitted by the second light source is caused by radiation of a wavelength range whose longest wavelength is at least 30 nm shorter compared to the shortest wavelength of the second wavelength transmission range of the at least one observation filter.

45. A medical optical system for observing fluorescent radiation in biological tissue, the system comprising:
- an illumination system having a light source and illumination optics, to illuminate the tissue with illumination radiation; and
- an imaging system having imaging optics, to guide radiation emanating from the tissue to an imaging plane;
- wherein the medical optical system further comprises a filter set comprising:
- at least one illumination filter arrangeable in the illumination system and having a first wavelength transmission range and a first wavelength blocking range comprising wavelengths longer than those comprised in the first wavelength transmission range; and
- at least one observation filter arrangeable in the imaging system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
- wherein a transmittance for wavelengths in the first wavelength transmission range and the second wavelength transmission range is greater than 0.5;
- wherein a transmittance for wavelengths in the first wavelength blocking range and the second wavelength blocking range is smaller than 0.5;
- wherein a product of the transmittance for wavelengths of the at least one illumination filter and the transmittance for wavelengths of the at least one observation filter in the second wavelength transmission range and the second wavelength blocking range is smaller than 0.05;
- wherein the at least one observation filter has a third wavelength transmission range comprising wavelengths shorter than those comprised in the second wavelength blocking range;
- wherein the transmittance for wavelengths of the at least one observation filter is greater than 0.01 in the third wavelength transmission range and is smaller than 0.01 in the second wavelength blocking range;
- wherein the second wavelength blocking range has a spectral width of at least 100 nm and
- wherein the first, the second and the third wavelength transmission ranges and the first and the second wavelength blocking range at least partially comprise the spectral range from 350 nm to 780 nm;
- wherein the illumination system comprises at least one filter holder in which the at least one illumination filter of the filter set is mounted; and
- wherein the imaging system comprises at least one filter holder in which the at least one observation filter of the filter set is mounted.

46. The medical optical system according to claim 45,
wherein the illumination system further comprises a second light source; and
wherein the central 90% of the intensity of the radiation emitted by the second light source is caused by radiation of a wavelength range whose longest wavelength is at least 30 nm shorter compared to the shortest wavelength of the second wavelength transmission range of the at least one observation filter.

47. A medical optical system for observing fluorescent radiation in biological tissue, the system comprising:
an illumination system having a light source and illumination optics, to illuminate the tissue with illumination radiation; and
an imaging system having imaging optics, to guide radiation emanating from the tissue to an imaging plane;
wherein the medical optical system further comprises a filter set comprising:
at least one illumination filter arrangeable in the illumination system and having a first wavelength transmission range and a first wavelength blocking range comprising wavelengths longer than those comprised in the first wavelength transmission range; and
at least one observation filter arrangeable in the imaging system and having a second wavelength transmission range comprising wavelengths longer than those comprised in the first wavelength transmission range of the at least one illumination filter and having a second wavelength blocking range comprising wavelengths shorter than those comprised in the second wavelength transmission range;
wherein a transmittance for wavelengths in the first wavelength transmission range and the second wavelength transmission range is greater than 0.5 and is, in the first wavelength blocking range and the second wavelength blocking range, smaller than 0.5;
wherein a product of the transmittance for wavelengths of the at least one illumination filter and the transmittance for wavelengths of the at least one observation filter is smaller than 0.05 in the second wavelength transmission range and the second wavelength blocking range;
wherein the at least one observation filter has a third wavelength transmission range comprising wavelengths shorter than those comprised in the second wavelength blocking range;
wherein the transmittance for wavelengths of the at least one observation filter in the third wavelength transmission range across a spectral width of at least 20 nm is greater than 0.001 and is smaller than 0.001 in the second wavelength blocking range;
wherein the second wavelength blocking range has a spectral width of at least 30 nm and
wherein the first, the second and the third wavelength transmission ranges and the first and the second wavelength blocking range at least partially comprise the spectral range from 350 nm to 780 nm;
wherein the illumination system comprises at least one filter holder in which the at least one illumination filter of the filter set is mounted; and
wherein the imaging system comprises at least one filter holder in which the at least one observation filter of the filter set is mounted.

48. The medical optical system according to claim 47,
wherein the illumination system further comprises a second light source; and
wherein the central 90% of the intensity of the radiation emitted by the second light source is caused by radiation of a wavelength range whose longest wavelength is at least 30 nm shorter compared to the shortest wavelength of the second wavelength transmission range of the at least one observation filter.

* * * * *